United States Patent [19]

Kim et al.

[11] Patent Number: 5,532,381

[45] Date of Patent: Jul. 2, 1996

[54] PROCESS FOR PREPARING PYRROLIZINE DERIVATIVES

[75] Inventors: Yong H. Kim, Seoul; Hee S. Park; Dong H. Lee, both of Taejeon, all of Rep. of Korea

[73] Assignee: Dong Kook Pharmaceutical Co., Ltd., Seoul, Rep. of Korea

[21] Appl. No.: 352,085

[22] Filed: Nov. 30, 1994

[30] Foreign Application Priority Data

Nov. 16, 1994 [KR] Rep. of Korea .................. 94-29968

[51] Int. Cl.$^6$ .................. C07D 451/00; C07D 487/04
[52] U.S. Cl. .................................. 548/453; 548/465
[58] Field of Search .................... 548/453, 465

[56] References Cited

U.S. PATENT DOCUMENTS

| | | | |
|---|---|---|---|
| 4,089,969 | 5/1978 | Muchowski et al. | 424/274 |
| 4,347,486 | 8/1982 | Muchowski et al. | 548/516 |
| 4,496,741 | 1/1985 | Doherty | 548/453 |
| 5,082,950 | 1/1992 | Muchowski et al. | 548/453 |
| 5,082,951 | 1/1992 | Muchowski et al. | 548/453 |

OTHER PUBLICATIONS

J. Med. Chem., 1985, vol. 28, pp. 1037–1049; J. M. Muchowski et al.: *Synthesis and Antiinflammatory and Analgesic Activity of 5–Aroyl–1,2–dihydro–3H–pyrrolo[1,2–a]pyrrole–1–carboxylic Acids and Related Compounds.*

Can. J. Chem., vol. 60, 1982, pp. 2295–2312; Humberto Caprio et al.: *Synthesis of 1,2–dihydro–3H–pyrrolo[1,2–a]pyrrole–1–carboxylic acids and homologous pyridine and azepine analogues thereof.*

J. Org. Chem., vol. 47, 1982, pp. 1682–1688; Fidencio Franco et al.: *Novel Syntheses of –Aroyl–1,2–dihydro–3H–pyrrole[1,2–a]pyrrole–1–carboxylic Acids.*

J. Org. Chem., vol. 44, No. 24, 1979, pp. 4410–4419; Bruce E. Maryanoff: *Carbenoid Chemistry, Reaction with Pyrrole Derivatives with Ehtyl Diazoacetate.*

J. Org. Chem., vol. 42, No. 26, 1977, pp. 4248–4251; Julian White et al.: *The Vilsmeier–Haack Aroylation of Pyrroles Reexamined.*

Primary Examiner—David B. Springer
Attorney, Agent, or Firm—Kenyon & Kenyon

[57] ABSTRACT

This invention relates to novel processes for preparing substituted pyrrolizine compounds. More particularly, it relates to novel processes for preparing [5-aroyl-2,3-dihydro-1H-pyrrolizine-1,1-dicarboxylate] of the following formula (I) from pyrrole.

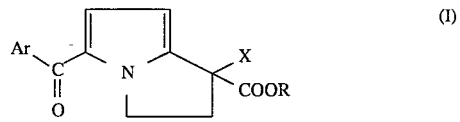

9 Claims, No Drawings

PROCESS FOR PREPARING PYRROLIZINE DERIVATIVES

BACKGROUND OF THE INVENTION i) Field of the Invention

This invention relates to novel processes for preparing substituted pyrrolizine compounds. More particularly, it relates to novel processes for preparing ⌈5-aroyl-2,3-dihydro-1H-pyrrolizine-1,1-dicarboxylate⌋ of the following formula (I) from pyrrole.

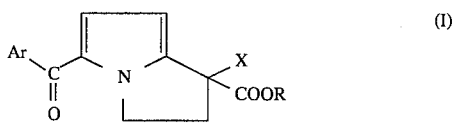

By hydrolysis and/or mono-decarboxylation from the compounds of formula (I), the useful anti-inflammatory agent and analgesic agent can be prepared.

ii) Description of the Prior Art 5-phenyl-2,3-dihydro-1H-pyrrolizine-1-carboxylic acid (hereinafter referred to as ketorolac) was first synthesized and patented under the U.S. Pat. No. 4,089,969 by Muchowsky in 1978. The following formula (II) and its pharmaceutically acceptable salts and esters are now under study as analgesic, anti-inflammatory and anti-pyretic agents for humans. Further, they can be also used for muscle relaxants.

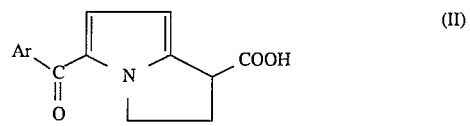

Currently, ketorolac has been marketed as useful a anti-inflammatory agent and analgestic agent in the United States, Italy, the Netherlands and other nations.

Various methods for preparing the pyrrolizine derivatives including ketorolac were disclosed by U.S. Pat. Nos. 4,347,186; 4,458,081; 4,347,187; 4,454,326; 4,347,185; 4,505,927; 4,456,759; 4,873,340; 4,496,741; 5,082,950 and 5,082,951.

In U.S. Pat. No. 4,317,186, a fundamental approach to the synthesis of 5-aroyl-2,3-dihydro-1H-pyrrolizine-1,1-dicarboxylates of formula (I) was disclosed. In this process, the crucial step was the intramolecular displacement of methanesulfinate ion by sodium malonates. However, this preparation method has some drawbacks due to its long reaction pathway and low yield of end product.

The following are reaction schemes of this method:

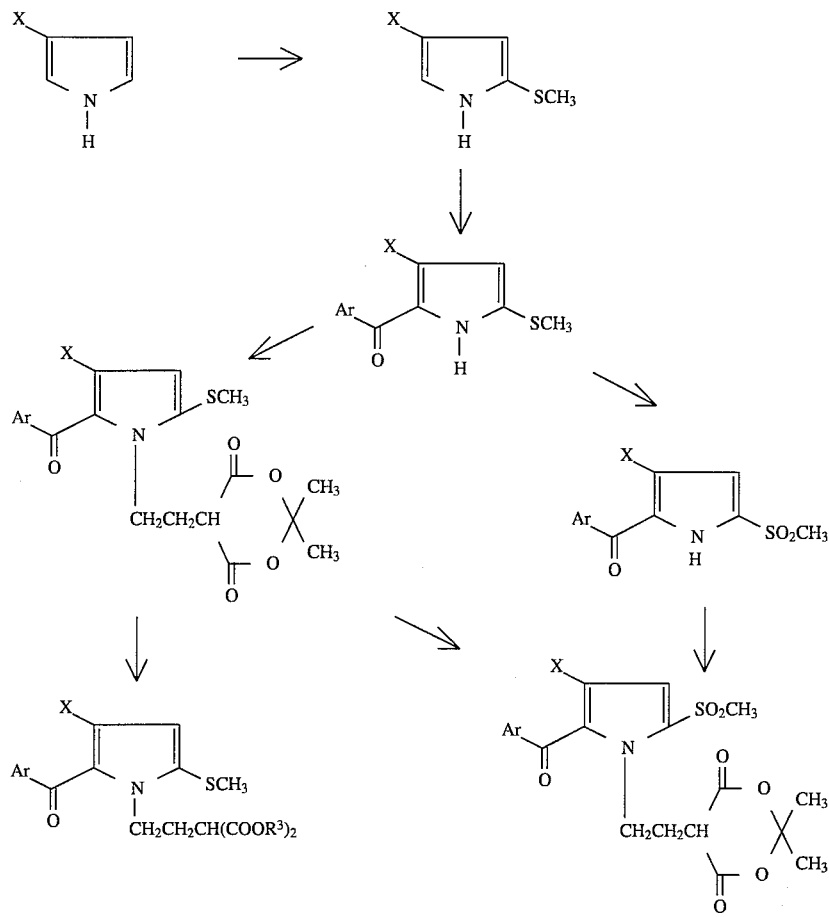

-continued

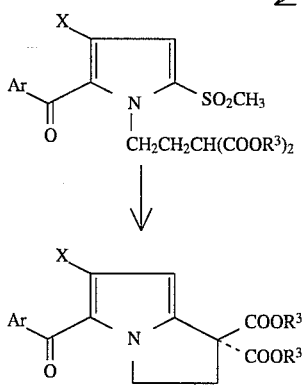

wherein
R³ and X are independently hydrogen or lower alkyl; and
Ar is a moiety selected from the group consisting of furyl or thienyl derivatives substituted by hydrogen, methyl, chloro or bromo; phenyl derivatives substituted by hydrogen, lower alkyl, lower alkoxycarbonyl, lower alkyl carbonyl, fluoro, chloro or bromo; and pyrrolyl derivatives substituted by hydrogen or lower alkyl.

Another method for preparing the compounds of formula (I) was disclosed in U.S. Pat. No. 5,082,950 by Muchowski using the intermolecular double alkylation reaction. However, it requires excessive reagents for the reaction, even though the reaction pathway becomes short.

The following are reaction schemes disclosed in U.S. Pat. No. 5,082,950:

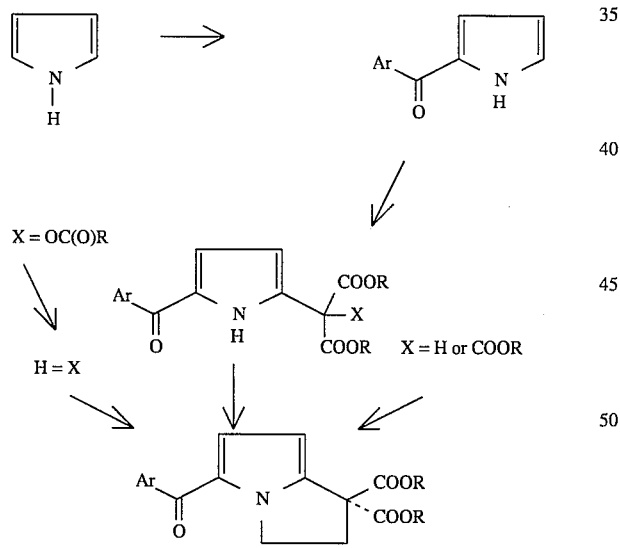

wherein
R is lower alkyl;
Ar is a moiety selected from the group consisting of phenyl derivatives substituted by lower alkyl, lower alkenyl, lower alkynyl, lower alkoxy, lower alkylthio, lower alkylsulfinyl, lower alkyl sulfonyl, dialkylamine, hydrogen, hydroxy, phenyl, phenyloxy, benzyl, benzoyl and nitro radical at any available position in the aromatic ring;
X is selected from the group consisting of alkoxycarbonyl, acyloxy and hydrogen.

SUMMARY OF THE INVENTION

The object of the present invention is to provide an improved process for preparing the compounds of formula (I).

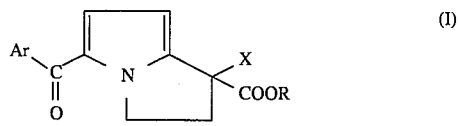 (I)

wherein
R is lower alkyl;
X is hydrogen or alkoxycarbonyl;
Ar is a moiety selected from the group consisting of

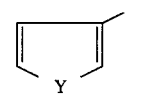

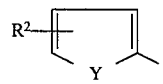

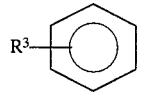

and

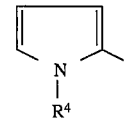

in which;
R² is hydrogen, methyl, chloro or bromo, the R² substitution being at the 3-, 4- or 5-position of the ring;
R³ is hydrogen, lower alkyl, lower alkoxycarbonyl, lower alkylcarbonyl, fluoro, chloro or bromo, the R³ substitution being at any available position in the ring;
R⁴ is hydrogen or lower alkyl;
Y is oxygen or sulfur.

Furthermore, the intermediate compounds in this invention are novel. Therefore, the present invention provides the novel intermediates in the process there in.

DETAILED DESCRIPTION OF THE INVENTION

Pyrrole is used as starting material. Dialkyl diazomalonate or alkyl diazoacetate is reacted with pyrrole in the presence of transition metal as promoting agent. As promoting agents, Cu, $Cu(OSO_2CF_3)_2$, $Cu\{O[C(O)CH_3]_2\}_2$, $Cu\{O[C(O)CF_3]_2\}_2$, or $Rh_2(OAc)_4$ can be preferably used. Carvene is formed intermediately by the reaction between alkyl diazoacetate and metal, and the formed carvene is reacted with pyrrole. And then, the useful intermediate, dialkyl pyrroyl malonate or alkyl pyrroyl acetate of formula (III), is prepared.

In the course of preparing the pyrrole derivatives of formula (III), remaining excessive pyrrole can be easily corrected after reaction. Furthermore, the amount of promoting agents required for this reaction is only 1% of the amount of diazo compounds in the equivalent ratio.

Therefore, the process of the present invention is more economical and shows better yields compared to known processes.

The intermediate compounds of formula (III) can be converted using two alternative reaction pathways into the compounds of formula (IV) or into the compounds of formula (V).

As a first reaction pathway, in order to synthesize the compounds of formula (VI), cyclization is made in the presence of small quantity of 1,2-dihaloalkane and potassium carbonate ($K_2CO_3$) as a base in aprotic polar solvent, e.g., tetrahydrofuran, DMF (dimethylformamide).

The compounds of formula (I) can be prepared according to the Vilsmeir-Haack aroylation using aryl morpholide-acid chloride complexes or dialkylamine-acid chloride complexes.

As another reaction pathway, the compounds of formula (V) can be prepared according to the Vilsmeir-Haack aroylation using arly morpholide-acid chloride complexes or dialkylamine-acid chloride complexes from compounds of formula (III). Obtained compounds are cyclized in the presence of a small quantity of 1,2-dihaloalkane and potassium carbonate as a base in aprotic polar solvent. Finally, the final-product of formula (I) is obtained.

Ketorolac and its pharmaceutically acceptable salts or esters can be easily prepared by the hydrolysis or monodecarboxylation of the compounds of formula (I).

The reaction pathways of the present invention can be represented schematically as follows:

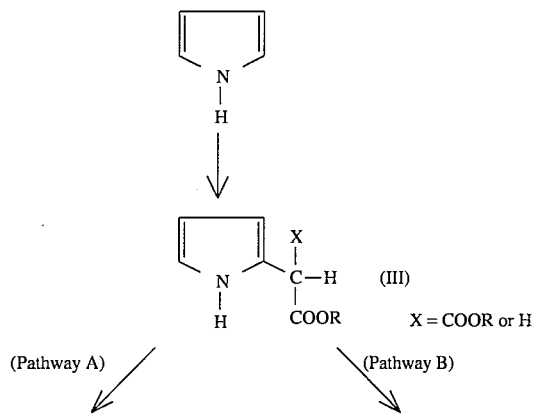

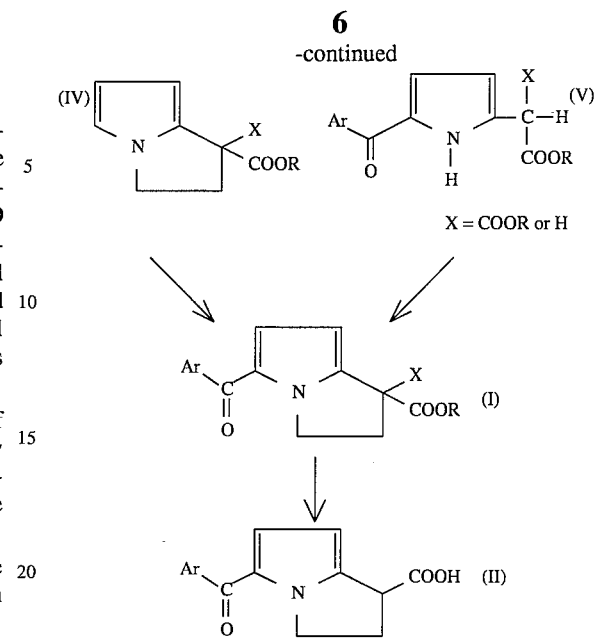

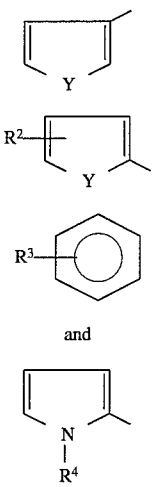

wherein
R is lower alkyl;
X is hydrogen or alkoxycarbonyl;
Ar is a moiety selected from the group consisting of in which;
$R^2$ is hydrogen, methyl, chloro or bromo, the $R^2$ substitution being at the 3-, 4- or 5-position of the ring;
$R^3$ is hydrogen, lower alkyl, lower alkoxycarbonyl, lower alkylcarbonyl, fluoro, chloro or bromo, the $R^3$ substitution being at any available position in the ring;
$R^4$ is hydrogen or lower alkyl; and
Y is oxygen or sulfur.

The present invention can be explained in more detail but is not limited to the following, but shall not be contrued to be limited by examples.

EXAMPLE 1

Preparation of Diethyl 2-Pyrroyl Malonate

Pyrrole (0.909 g, 13.5 mmole) and $CU\{O[C(O)CF_3]_2\}_2$ (22.3 mg, 0.045 mmole) were placed in a flask and heated at 80° C. in oil bath while stirring. Diethyl diazomalonate (0.784 g, 4.5 mmole) was added drop by drop to the flask, and the mixture was heated for an hour. The reaction mixture was distilled using a Kugelrohr Distillation Apparatus under 0.1 torr pressure at 90° C. Finally, a pale yellow liquid of the product ⌈diethyl 2-pyrroyl malonate⌋ (0.779 g, 77%) was obtained. The excessive pyrrole remaining without reaction was collected quantitatively.

1H NMR (CDCl$_3$): δ9.07(NH), 6.78(dd, 1H), 6.13(dd, 2H), 4.23(s, 1H), 4.18(g, 4H), 1.26(t, 6H)

EXAMPLE 2

Preparation of Diethyl 2,3-Dihydro-1H-Pyrrolizine-1,1-Dicarboxylate

A mixture of diethyl-2-pyrroyl malonate (225 mg, 0.1 mmole), dibromoethane (188 mg, 0.5 mmole) and potassium carbonate (138 mg, 0.5 mmole) was stirred and reacted in 5 ml of DMF for 2 hours at 80° C. After removing the solvent, the reaction residue was purified by silica gel column chromatography using ethyl acetate-hexane (1:9) as an eluting solvent. Finally, the product ⌈diethyl 2,3-dihydro-1H-pyrrolizine-1,1-dicarboxylate⌋ (239 mg, 95%) was obtained.

1H NMR (CDCl$_3$): δ6.60(m, 1H), 6.23~6.09(m, 2H), 4.21(q, 4H), 4.07(t, 2H) 3.02(t, 2H), 1.25(t, 6H)

EXAMPLE 3

Preparation of Diethyl(5-Benzoylpyrrole-2-yl)Methanedicarboxylate

A solution of N,N-dimethylbenzamide (60 mg, 0.4 mmole) and POCl$_3$ (61 mg, 0.4 mmole) dissolved in 2 ml of 1,2-dichloroethane was refluxed for one hour. A solution of diethyl-2-pyrroylmalonate (45 mg, 0.2 mmole) dissolved in 1 ml of 1,2-dichloroethane was added and refluxed for 5 hours. The reacted material was cooled at room temperature and diluted with 4 ml of 1,2-dichloroethane. A solution of 500 mg of NaOAc dissolved in 2 ml of water was added. The final mixture was refluxed for 2 hours, and the organic layer was separated. The organic layer was washed with a saturated NACl solution and dried with MgSO$_4$. After treating with active carbon, the solvent was removed under reduced pressure. The residue was isolated by silica gel column chromatography using ethyl acetate-hexane (1:9) as an eluting solvent, and 41 mg of the product ⌈diethyl(5-benzoylpyrrole-2-yl)methanedicarboxylate⌋ (61%) was finally obtained.

1H NMR (CDCl$_3$): δ10.16(s, 1H), 7.88~7.40(m, 5H), 6.78(dd, 1H), 6.27(dd, 1H), 4.79(s, 1H), 4.25(q, 4H), 1.25(t, 6H)

EXAMPLE 4

Preparation of Diethyl 5-Benzoyl-2,3-Dihydro-1H-Pyrrolizine-1,1-Dicarboxylate

A mixture of POCl$_3$ (166 mg, 1.08 mmole) and N-benzoylmorpholine (96 mg, 0.5 mmole) was maintain for 6 hours at 25° C. A solution of diethyl-2,3-dihydro- 1H-pyrrolizine-1,1-dicarboxylate (126 mg, 05 mmole) in dichloroethane (2 ml) was added. Then, the mixture was maintained at 50° C. for 3 days. The reacted mixture was poured with 2.5 ml of 10% aqueous sodium carbonate solution. The mixture was stirred at room temperature for 10 hours, and refluxed for 2 hours. The organic layer was separated, and the aqueous layer was washed with 1,2-dichloroethane. The organic layer was dried using sodium carbonate, and the solvent was removed. Finally, the residue was purified by silica gel column chromatography using ethyl acetate-hexane (1:9) as an eluting solvent and 178 mg of the product ⌈diethyl 5-benzoyl-2,3-dihydro-1H-pyrrolizine-1,1 -dicarboxylate⌋ (84%) was obtained. The IR and NMR spectral properties were identical to those of an authentic sample.

EXAMPLE 5

Preparation of Diethyl 5-Benzoyl-2,3-Dihydro-1H-Pyrrolizine-1,1-Dicarboxylate

A mixture of diethyl(5-benzoylpyrrole-2-yl)methane dicarboxylester (45 mg, 0.136 mmole), dibromoethane (0.058 mg, 0.68 mmole) and calcium carbonate (53 mg, 0.38 mmole) dissolved in 1.5 ml of DMF was stirred and reacted for 2 hours at 80° C. After removing the solvent, the reaction residue was purified by silica gel column chromatography using ethyl acetate-hexane as an eluting solvent. Finally, 45 mg of the product ⌈diethyl 5-benzoyl-2,3 -dihydro-1H-pyrrolizine-1,1-dicarboxylate⌋ (95%) was obtained. The IR and NMR spectral properties were identical to those of an authentic sample.

EXAMPLE 6

Preparation of 5-Benzoyl-2,3-Dihydro-1H-Pyrrolizine-1-Carboxylic Acid

A mixture of diethyl 5-benzoyl-2,3-dihydro-1H-pyrrolizine-1,1dicarboxylester (21 mg, 0.06 mmole) dissolved in 1 ml of diethylether and 20% sodium hydroxide solution(0.35 ml) was stirred and refluxed for 24 hours. The aqueous layer was washed with ether(1 ml), and acidified with concentrated hydrochloric acid. Then, the aqueous layer was washed with ethyl acetate, and the extracted material was heated for 4 hours at 70° C. Finally, the ethyl acetate solution was concentrated under reduced pressure to yield a final product ⌈5-benzoyl-2,3-dihydro-1H-pyrrolizine-1-carboxylic acid⌋ (4 mg, 93%) as a pure solid.

We claim:

1. A process for preparing compounds of formula (I)

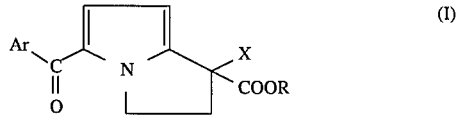

wherein

R is lower alkyl,

X is hydrogen or alkoxycarbonyl,

Ar is a moiety selected from the group consisting of

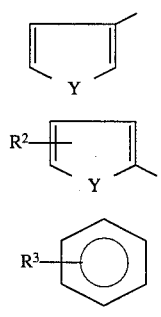

and

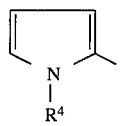

in which

R² is hydrogen, methyl, chloro or bromo, the R² substitution being at the 3-, 4- or 5-position of the ring, R³ is hydrogen, lower alkyl, lower alkoxycarbonyl, lower alkylcarbonyl, fluoro, chloro or bromo, the R³ substitution being at any available position in the ring, R⁴ is hydrogen or lower alkyl, Y is oxygen or sulfur, comprising the steps of:
i) preparing compounds of formula (III)

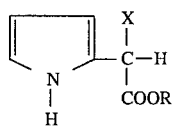
(III)

by the reaction between pyrrole and dialkyl diazomalonate or alkyl diazoacetate in the presence of a transition metal or an organometallic transition metal compound as a promoting agent;

ii) preparing compounds of formula (IV)

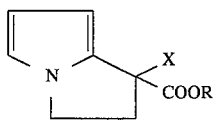
(IV)

by the reaction between the compounds of formula (III) and dihaloethane in the presence of potassium carbonate as a base in an aprotic polar solvent; and iii) preparing the compounds of formula (I) according to Vilsmeir-Haak aroylation using arylmorpholide-acid chloride complexes or dialkyl amine-acid chloride complexes.

2. A process for preparing compounds of formula (I)

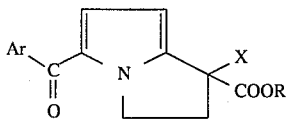
(I)

wherein

R is lower alkyl,

X is hydrogen or alkoxycarbonyl,

Ar is a moiety selected from the group consisting of

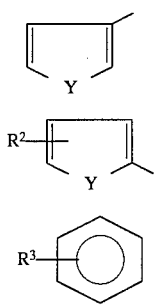

and

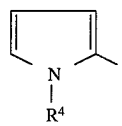

in which

R² is hydrogen, methyl, chloro or bromo, the R² substitution being at the 3-, 4- or 5-position of the ring, R³ is hydrogen, lower alkyl, lower alkoxycarbonyl, lower alkylcarbonyl, fluoro, chloro or bromo, the R³ substitution being at any available position in the ring, R⁴ is hydrogen or lower alkyl, Y is oxygen or sulfur, comprising the steps of:
i) preparing compounds of formula (III)

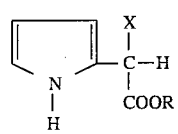
(III)

by the reaction between pyrrole and dialkyl diazomalonate or alkyl diazoacetate in the presence of a transition metal or an organometallic transition metal compound as a promoting agent;

ii) preparing compounds of formula (V)

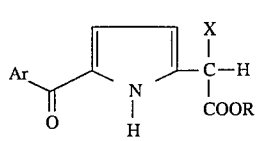
(V)

according to Vilsmeir-Haak aroylation using arylmorpholide-acid chloride complexes or dialkyl amine-acid chloride complexes; and (iii) preparing compounds of formula (I) by the reaction between compounds of formula (V) and dihaloethane in the presence of potassium carbonate as a base in an aprotic polar solvent.

3. A process for preparing the compounds of formula (I) according to claim 1, wherein Ar is phenyl and R is ethyl.

4. A process for preparing the compounds of formula (I) according to claim 1, wherein said promoting agent is selected from the group consisting of Cu, Cu(OSO₂CF₃)₂, Cu{O[C(O)CH₃]₂}₂, Cu{O[C(O)CF₃]₂}₂, and Rh₂(OAc)₄.

5. A process for preparing the compounds of formula (I) according to claim 1, wherein said aprotic polar solvent is tetrahydrofuran or dimethylformamide.

6. A process for preparing the compounds for formula (I) according to claim 4, wherein the required amount of promoting agent is 1% of diazo compounds in the equivalent ratio.

7. A process for preparing the compounds of formula (I) according to claim 2, wherein Ar is phenyl and R is ethyl.

8. A process for preparing the compounds of formula (I) according to claim 2, wherein said promoting agent is selected from the group consisting of Cu, Cu(OSO₂CF₃)₂, Cu{O[C(O)CH₃]₂}₂, Cu{O[C(O)CF₃]₂}₂, and Rh₂(OAc)₄.

9. A process for preparing the compounds of formula (I) according to claim 2, wherein said aprotic polar solvent is tetrahydrofuran or dimethylformamide.

* * * * *

UNITED STATES PATENT AND TRADEMARK OFFICE
CERTIFICATE OF CORRECTION

PATENT NO. : 5,532,381
DATED : July 2, 1996
INVENTOR(S) : Yong H. Kim, et al

It is certified that error appears in the above-indentified patent and that said Letters Patent is hereby corrected as shown below:

| Column | Line | |
|---|---|---|
| 2 | 9 | Change "useful a" to --a useful--. |
| 4 | 67 | Change "there in" to --therein--. |
| 6 | 57 | After "detail" insert --by,--. |
| 6 | 58 | After "limited to" insert --,--; after "following" delete ", but shall not be contrued to". |
| 6 | 59 | Delete "be limited by". |
| 7 | 41 | Change "NACl" to --NaCl--. |
| 7 | 58 | Change "maintain" to --maintained--. |

Signed and Sealed this

Sixteenth Day of September, 1997

Attest:

BRUCE LEHMAN

*Attesting Officer*  *Commissioner of Patents and Trademarks*